United States Patent [19]

Abe et al.

[11] Patent Number: 4,895,722
[45] Date of Patent: Jan. 23, 1990

[54] HAIR TREATMENTS

[75] Inventors: Yoshiaki Abe, Tokyo; Rikio Tsushima, Wakayama; Hiroshi Watanabe, Funabashi, all of Japan

[73] Assignee: Kao Soap Co., Ltd., Tokyo, Japan

[21] Appl. No.: 645,532

[22] Filed: Aug. 29, 1984

Related U.S. Application Data

[63] Continuation of Ser. No. 352,463, Feb. 25, 1982, abandoned.

[30] Foreign Application Priority Data

Mar. 3, 1981 [JP] Japan ................... 56-30275

[51] Int. Cl.$^4$ ................ A61K 7/06; A61K 7/09; A61K 7/11
[52] U.S. Cl. ....................... 424/71; 424/70; 424/72; 424/DIG. 1; 424/DIG. 2
[58] Field of Search ............. 424/71, 72, DIG. 1, 424/DIG. 2, 70

[56] References Cited

U.S. PATENT DOCUMENTS

| | | | |
|---|---|---|---|
| 3,912,808 | 10/1975 | Sokol | 424/72 |
| 3,957,065 | 5/1976 | Busch et al. | 424/72 |
| 3,958,581 | 5/1976 | Abegg et al. | 424/71 |
| 4,041,150 | 8/1977 | Karjala | 424/71 |
| 4,201,766 | 5/1980 | Grollier et al. | 424/71 |
| 4,436,722 | 3/1984 | Matsunaga et al. | 424/72 |
| 4,465,664 | 8/1984 | Matsunaga et al. | 424/72 |
| 4,495,173 | 1/1985 | Matsunaga et al. | 424/70 |

*Primary Examiner*—Douglas W. Robinson
*Attorney, Agent, or Firm*—Oblon, Spivak, McClelland, Maier & Neustadt

[57] ABSTRACT

A hair treatment comprising in dissolved form three essential components including at least one decomposition derivative of keratin, a cationic polymer, and at least one compound selected from organic and inorganic salts and urea having a solubility in water of over 1 g/100 g of water at 25° C. The hair treatment within the scope of the invention covers various types of treatments such as hair setting lotion, hair styling lotion, cutting lotion, brushing lotion and the like.

5 Claims, No Drawings

HAIR TREATMENTS

This application is a continuation of application Ser. No. p352,463 filed Feb. 25, 1982, now abandoned.

BACKGROUND OF THE INVENTION

1. Field of the Invention

This invention relates to the cosmetic art of hair and, more particularly, to hair treatments which can impart so-called steadiness and firmness to the hair and exhibit excellent touch when they are applied to the hair

2. Description of the Prior Art

The hair is one of the most important parts of human body, on which a diversity of beauty treatments are applied. Among the beauty treatments, the permanent wave treatment is a well-known beauty art and is most effective in setting the hair properly. However, this treatment has the drawback that since oxidation and reduction reactions are utilized to set the hair, the hair is considerably damaged during the treatment.

In recent years, there has been a demand for the development of hair treatments which can effectively set the hair without resorting to any permanent wave art. Various methods have been proposed including, for example, a method of reinforcing the hair using combinations of quaternary ammonium salts, cationic polymers and harmless divalent metals (Japanese Laid-open Application No. 55-54551), a method in which water-soluble salts of chitosan are used as fill-forming resin to improve the retentivity and stability of dressed hair (Japanese Laid-open Application No. 52-156938), and a method wherein anionic polymers and cationic surface active agents and silicone derivatives are used in combination to impart high set retentivity and curl durability to hair (Japanese Laid-open Application No. 55-108811) and the like.

However, although all of these methods are effective in imparting steadiness and firmness to the hair at the time of setting the hair, they have the disadvantage that the hair treated becomes stiff, considerably impeding the inherent touch of hair.

Further, there has been proposed a method using oils which are one starting material of cosmetics but such a method is no widely applied because of the stickiness of oil.

SUMMARY OF THE INVENTION

It is an object of the invention to provide hair treatments which can impart smoothness and softness to the hair and exhibit excellent touch on application without showing undesirable stickiness.

It is another object of the invention to provide hair treatments which exhibit good affinity for hair as will not be experienced in prior-art counterparts.

The above objects can be achieved, according to the invention, by hair treatments which comprises the following three ingredients (A), (B) and (C):

(A) 0.05 to 10 wt % of at least one decomposition derivative of keratin;

(B) 0.05 to 10 wt % of a cationic polymer; and (C) 0.01 to 10 wt % of at least one compound which has a solubility in water of over 1 g/100 g of water at 25° C. and selected from the group consisting of organic and inorganic salts and urea.

DETAILED DESCRIPTION OF THE PREFERRED EMBODIMENTS

The decomposition derivatives of keratin to be ingredient (A) used in the present invention can be prepared by any of the methods including a method of oxidizing keratin materials for decomposition and converting them into alkali salts, a method of reducing keratin materials for decomposition, chemically modifying the thiol groups of the reduction product, and converting the modified product into alkali salt, and a method of hydrolyzing keratin materials.

The starting keratin materials are, for example, animal hairs, human hair, feathers, nails, horns, hooves, scales and the like, among which wool, human hair and feathers are most preferable. These keratin materials can be subjected to the oxidation or reduction reaction as they are but may be cut or reduced into pieces or subjected to pretreatments such as washing and defatting, if necessary.

The decomposition of keratin material can be carried out by any of the following methods.

(1) Oxidation and Decomposition Reaction

The oxidation of keratin material is effected by any of methods known per se (N.H. Leon; Textile Progress, Vol. 7, page 1 (1975). Oxidizing agents are preferably of the type which may be either organic or inorganic but acts electrophilically on the disulfide bonds (S-S bonds) in the keratin structure. Examples of the oxidizing agents include organic peracids, inorganic peroxo acids or their salts, permanganic acid or its salts, chromic acid or related compounds, halogens, peroxides, oxyacids or their salts and the like, among which organic peracids such as peracetic acid, performic acid and perbenzoic acid are most preferable.

The oxidation reaction is carried out in liquid medium using oxidizing agents in excess with respect to the disulfide bonds in keratin material, ordinarily in amounts over two equivalents or more, preferably 4 to 10 equivalents, of the sulfide bonds. The reaction may be conducted under acidic or alkaline conditions and is preferably carried out under acidic and particularly weakly acidic conditions. The conditions such as reaction temperature and pressure depend on the types of the oxidizing agent and keratin material used and are not critical. In general, the reaction temperature is sufficiently room temperature but, if necessary, heat may be applied. The pressure is a normal pressure but the reaction may be effected under reduced pressure or pressure.

By this, the disulfide bonds of keratin material are cleft into sulfonic acid (—$SO_3H$).

(2) Reduction decomposition and Chemical Modification Reactions

Reducing agents employed for reducing keratin materials are preferably organic or inorganic reducing agents of the type which are capable of cleaving the disulfide bond in the keratin structure into a thiol group (—SH) and act nucleophilically on the disulfide bond. Examples of the reducing agent include organic reducing agents such as mercaptoethanol, thioglycollic acid, benzylmercaptan, 1,4-dithiothreitol, tributylphosphine and the liked, and inorganic reducing agents such as sodium hydrogensulfite, sulfides such as sodium hydrogensulfide, metallic hydrides such as lithium aluminium hydride, and the like.

The amount of the reducing agent is usually in the range of 2 to 10 equivalents of the disulfide bonds in keratin material. The reaction system has generally a pH range of 2 to 12, preferably 6 to 11. Outside the range, the hydrolysis undesirably takes place at the same time. The reaction temperature is sufficiently room temperature but heat may be applied to shorten the reaction time. The reaction time is ordinarily in the range of 2 to 3 hours or more. Since it is necessary that the thiol groups produced by the reaction do not substantially undergo oxidation, the reduction operation should favorably be carried out in a atmosphere of inert gas to give good results.

The decomposition product obtained by the reduction of keratin material is then chemically modified at the thiol groups thereof to obtain a derivative thereof. The derivatives at the thiol groups include:

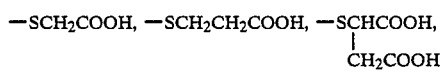

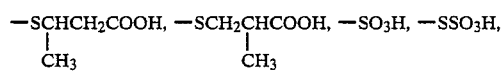

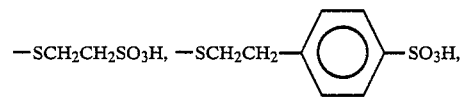

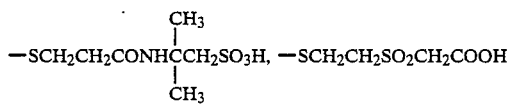

among which

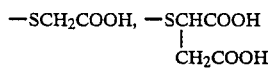

are preferable.

The chemical modification of thiol group is feasible by any techniques known per se and can be effected according to procedures known, for example, from N. H. Leon; Textile Progress, Vol. 7 (1975), "Yuuki Ioo Kagobutsu (Organic Sulfur Compounds)" written by Shigeru Daikyo and published by Kagaku Dojin (1968), and "Kobunshi Jikken Koza" written by Masami Oku, Vol. 12, Kyoritsu Shuppan (1957). Typical methods are described in the following.

1. Method utilizing the nucleophilic substitution reaction of SH group $$K-SH + R-L \rightarrow K-S-S-R + HL$$

(in which K re a residue of keratin material, R represents a chemically modifying group to be introduced, and L represents a leaving atom or group such as a halogen atom or an acid residue). Compounds reacting by this method include, for example, halogen compounds such as iodoacetic acid, bromoacetic acid, chloroacetic acid and the like.

2. Method utilizing the nucleophilic addition reaction of SH group with a double bond existing between carbon atoms

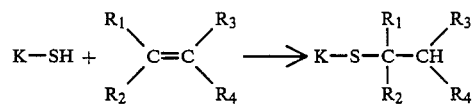

(in which at least one of $R_1$, $R_2$, $R_3$ and $R_4$ represents a group having a carboxyl group or sulfonic acid group therein and the others independently represent an alkyl group or hydrogen atom, and K has the same meaning as defined above).

Compounds reacting by this method include, for example, acrylic acid, methacrylic acid, crotonic acid, maleic acid, fumaric acid, vinylcarboxymethylsulfone, vinylsulfonic acid, styrenesulfonic acid, 2-acrylamido-2-methylpropansulfonic acid and the like.

3. Method using the substitution reaction between the SH group and sulfite compounds

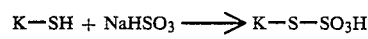

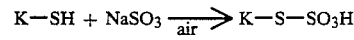

(in which K has the same meaning as defined hereinabove).

4. Method of oxidizing SH group into sulfonic acid group

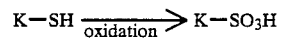

(in which K has the same meaning as defined hereinabove).

The oxidizing agents to be used in this reaction include, for example, halogens, permanganates and the like.

(3) Hydrolysis Reaction

1. Hydrolysis with Acid

Mentioned as acid are, for example, inorganic acids such as hydrochloric acid, sulfuric acid, phosphoric acid, nitric acid, hydrobromic acid and the like, and organic acids such as acetic acid, formic acid, oxalic acid and the like. These acids are generally employed at a concentration of 3 to 85% and it is desirable that the hydrolysis reaction is invariably caused to proceed at a pH below 4. The reaction temperature is preferably in the range of 40 to 100° C. though it may be raised up to 160° C. under pressure. The reaction time is conveniently in the range of 2 to 24 hours. The reaction product may be used as it is after neutralization with alkalis such as sodium hydroxide, sodium carbonate, ammonia and the like. Alternatively, it may be used after subsequent purification such as by gel filtration and ion exchange resin.

The products obtained by the hydrolysis with acid involve no changes other than hydrolysis given to the polypeptide chains of keratin, so that better results are obtained than those of products obtained by hydrolysis with alkali.

2. Hydrolysis with Alkali

As alkalis, there are used inorganic alkalis such as sodium hydroxide, potassium hydroxide, lithium hydroxide, barium hydroxide, sodium carbonate, potassium carbonate, lithium carbonate, sodium silicate, borax and the like. These alkalis are conveniently used at a concentration of 1 to 20%. Larger amounts than as required are unfavorable because the resulting hydrolysate solution becomes brown or black in color. The reaction is preferably carried out at a temperature of room temperature to 100° C. for a time of 30 minutes to 24 hours. Care should be taken not to make the temperature higher and the reaction time longer is required. As the hydrolysis reaction with alkali proceeds, the hydrolysate of keratin is allowed to dissolve out with the attendant advantage that how far the reaction proceeds can visibly be observed. The reaction is completed at the time when the reaction mixture has turned into a uniform solution 3. Hydrolysis with Enzyme Examples of enzymes include acidic protenases such as pepsin protease A, protease B and like, and neutral protenases such as papain, promeline, thermolycin, trypsin, pronase, chymotrypsin and the like. The pH at the time of the hydrolysis should preferably be controlled in the range of 1 to 3 for the acidic protenases such as pepsin and in the range of 5 to 8 for the neutral protenases such as papain. It is convenient to properly adjust the pH by the use of an ammonium·acetate/ammonia buffer solution. The reaction temperature is favorably in the range of 30 to 45° C. and the reaction time is ordinarily in the range of 3 to 24 hours.

In the hydrolysis reaction with enzymes, the molecular weight of hydrolysate is greatly influenced by the amount of enzyme, the reaction temperature and the reaction time. In order to obtain a keratin hydrolysate with an intended molecular weight, it is necessary to check by the gel filtration technique the distribution of molecular weight of hydrolysate in relation to variations in amount of enzyme, reaction temperature and reaction time whereby the optimum conditions are empirically determined.

The hydrolysates obtained from enzyme show a narrower distribution of molecular weight than hydrolysates obtained from acid or alkali and contain reduced amounts of free amino acids, thus being fore favorable for use as cosmetics.

The hydrolsates should preferably contain in the structure thereof disulfide bonds in amounts as much as possible. To this end, it necessary to use keratin materials of high purity and to effect the hydrolysis reaction under mild conditions.

The decomposition products obtained by these decomposition methods should preferably have an average molecular weight of 30,000 to 100,000 for the products obtained by the method (1) or (2) and an average molecular weight of 200 to 5,000 for the product obtained by the method (3).

The decomposition product obtained by the method (3) is soluble in ordinary polar solvents such as water, ethanol, methanol, ethylene glycol, propylene glycol, glycol and the like and can be formulated in a pre-shampoo treatment of the present invention as a decomposition derivative of keratin material. In this connection, however, the products obtained by the methods (1) and (2) are insoluble in polar solvents and should be formulated after conversion into corresponding alkali salts. Alkali salts include salts of alkali metals such as sodium, potassium and the like, ammonium salts, and salts of organic bases such as ethanolamine, diethanolamine, triethanolamine, 2-amino-2-methylpropanol, aminomercaptopropanediol, triisopropanolamine, glycine, histidine, alginine, and the like. These salts can be prepared separately and then added to pre-shampoo treatments. Alternatively, the oxidation decomposition product or reduction derivative of keratin material and alkaline materials may be added to a pre-shampoo treatment wherein they are converted into a salt thereof. Examples of the alkaline material include inorganic alkaline materials such as sodium hydroxide, potassium hydroxide, sodium carbonate, potassium carbonate and the like, and organic alkaline materials such as ammonia, ethanolamine, diethanolamine, trietholaine, 2-amino-2-methyl-1-propanol, 2-amino-2-methyl-1,3-propanediol, 2-amino-2-methyl-1-propanol, 2-amino-2-ethyl-1,3-propanediol, 2-amino-1-butanol, triisopropanolamine, diisopropanol-amine, monoisopropanolamine, lysine, alginine, histidine, hydroxylysine and the like. These alkaline materials are preferably added in an amount of 0.1 to 8 equivalents of the carboxyl groups or sulfonic acid groups in the decomposition product obtained by the method (1) or (2).

Among these components of (A), the alkali salts of the oxidation decomposition product of keratin and the derivatives at the thiol groups of the reduction decomposition products of keratin are most preferable. The amount of the component (A) is, as having defined hereinbefore, in the range of 0.05 to 10.0 wt % (hereinafter referred to simply as preferably 0.1 to 2.0%, of the pre-shampoo treatment composition.

The component (B) of the present invention is polymers having an average molecular weight of 500 to 5,000,000 and having cationic groups in the main chain or substituent thereof. Preferable examples are shown below. (1) Quaternarized derivatives of cellulose ethers Examples of these derivatives are those obtained by quaternarizing cellulose ethers such as hydroxyethyl cellulose, methyl cellulose, ethyl cellulose, hydroxypropyl cellulose, hydroxypropyl methyl cellulose and the like, for example, with a cationizing agent such as glycidyltrimethylammonium chloride. Mentioned as a commercially available product is JR-400 (molecular weight 100,000 to 1,000,000; Union Carbide Co.).

(2) Cyclic cationic group-containing polymers

1. Diallyl quaternary ammonium homopoly recurring units of the formula (I) or (II)

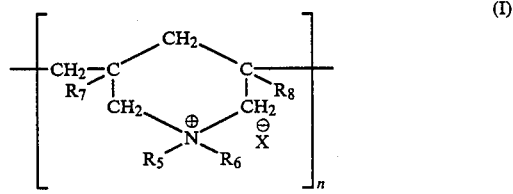

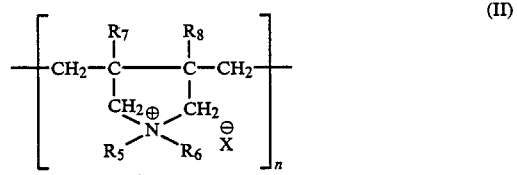

in which $R_5$ and $R_6$ are the same or different and represent hydrogen or an alkyl group having 1 to 18 carbon atoms, atoms, $R_7$ and $R_8$ are the same or preferably 1 to 4 carbon different and independently represent hydrogen, an alkyl group having 1 to 3 carbon atoms, or phenyl group, X represents an anionic residue, i.e. a halogen ion such as chlorine, bromine or the like, an inorganic acid residue such as sulfuric acid, nitric acid or the like, an organic acid residue such as methylsulfuric acid, hydroxycarboxylic acid or the like, and n is a value sufficient to give a molecular weight of 10,000 to 1,000,000.

2. Polymers of recurring units of the formula (III) or

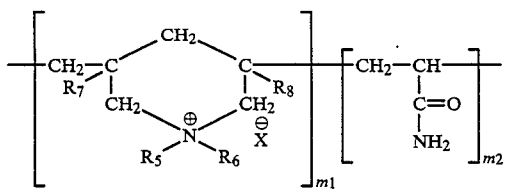

(III)

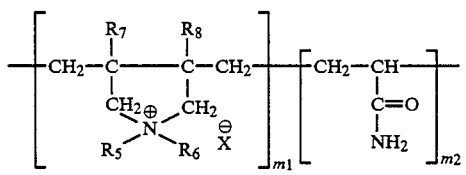

(IV)

(in which $m_1$ and $m_2$ are values sufficient to give a molecular weight of 10,000 to 1,000,000, and $R_5$, $R_6$, $R_7$ and $R_8$ have the same meanings as defined above, respectively).

3. Polymers of the formula (V)

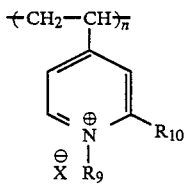

(V)

(in which $R_9$ and $R_{10}$ are the same or different and independently represent hydrogen, an alkyl group having 1 to 6 carbon atoms, or a phenyl group, and n and X have the same meanings as defined hereinbefore, respectively).

Among these cyclic cationic group-containing polymers, preferable polymers are a homopolymer of dimethyldiallylammonium chloride commercially sold as MERQUAT 100 (MERCK Inc.) and a copolymer of dimethyldiallylammonium chloride and acrylamide commercially available in the name of MERQUAT 550 (MERCK Inc.).

(3) Quaternarized derivatives of copolymers of N-vinylpyrrolidone/vinyl monomer

Quaternarized derivatives of copolymers of N-vinylpyrrolidone/vinylmonomer of the formula (VI)

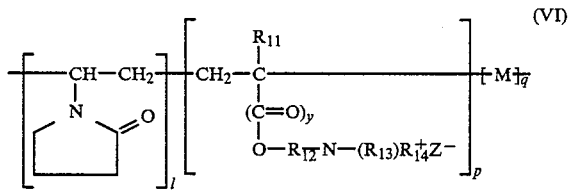

(VI)

(in which l, p and q are values which are determined such that the monomer units in the respective brackets are, respectively, 20 to 99 mole %, 1 to 80 mole % and 0 to 50 mole %, y is 1 or 0, $R_{11}$ represents a hydrogen atom or methyl group, $R_{12}$ represents

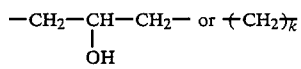

(wherein K is a value of 2 to 18), $R_{13}$ represents an alkyl group having 1 to 4 carbon atoms and preferably —CH$_3$, —C$_2$H$_5$ or t-butyl group, $R_{14}$ represents

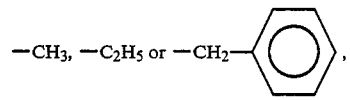

Z represents chlorine, bromine, iodine, SO$_4$, HSO$_4$ or CH$_3$SO$_3$, and M represents a monomer unit of a copolymerizable vinyl monomer).

This quaternarized copolymer can be prepared by copolymerizing N-vinylpyrrolidone, a dialkyl(lower)aminoalkyl (or hydroxyalkyl)acrylate (or methacrylate) and other arbitrary copolymerizable vinyl monomer. The proportions by mole % of the unit monomers are as follows: the vinylpyrrolidone unit is 20 to 99%, the dialkyl(lower)aminoalkyl(or hydroxyalkyl)acrylate(or methacrylate) unit is 1 to 80%, and the other copolymerizable vinyl monomer unit is in the range of 0 to 50%.

The molecular weight of this terpolymer is generally in the range of 15,000 to 1,000,000, preferably 50,000 to 500,000.

Mentioned as commercially available products are GAFQUAT 734 (average molecular weight of about 100,000 GAF Co., Ltd.) and GAFQUAT 755 (average molecular weight of about 1,000,000, GAF Co., Ltd.).

The content of the component (B) in the hair treatment is in the range of 0.05 to 10%, preferably 0.1 to 2%, as defined hereinbefore.

The component (C) used in the present invention is at least one member selected from inorganic or organic salts and urea having a solubility in water of over 1g/100 g of water at 25° C. (hereinafter referred to generically as water-soluble salt). The inorganic or organic salts should preferably have a solubility in water of 10 to 100 g/100 g of water of 25° C. Examples of these inorganic or organic salts include inorganic ammonium, alkali metal and alkaline earth metal salts such as aluminium sulfate, barium chloride, calcium carbonate, calcium chloride, magnesium nitrate, magnesium sulfate, copper sulfate, potassium phosphate, potassium thiocyanate, sodium chloride, lithium chloride, ammonium bicarbonate, ammonium nitrate, sodium sulfate and the like, and organic salts of alkali metals and organic acids such as sodium lactate, sodium benzoate, sodium citrate and the like. Of these, preferable salts are sodium chloride, potassium thiocyanate, sodium sulfate, potassium hydrogenphosphate, sodium lactate, sodium benzoate, and sodium citrate.

This component (C) is an essential one for achieving the purpose of the present invention and when this component is substituted with a known adjuvant such as, for example, ethanol, glycerine, propylene glycol or the like, the above purpose cannot be attained.

The amount of the component (C) in the hair treatment should be sufficient to dissolve the anionic material or component (A) and the cationic material or component (B) and is generally in the range of 0.01 to 10%, preferably 0.1 to 3%, as defined hereinbefore.

The hair treatment according to the invention is prepared by mixing these three components by a usual manner whereby various types of treatments such as hair setting lotion, hair styling lotion, cutting lotion, brushing lotion, hair spray, permanent wave lotion, hair dye, decolorant, shampoo, hair conditioner, hair rinse and the like can be obtained.

As a matter of course, the hair treatment according to the invention may be further incorporated with various arbitrary ingredients including, for example, surface active agents such as alkyl sulfates, fatty acid salts, polyoxyethylene alkylamidosulfates, α-olefinsulfates, alkyltrimethylammonium salts, alkyldimethylammonium salts, N-alkylbetaines, N-alkylamidobetaines, alkylmidazolines, polyoxyethylene alkyl ethers, polyoxyethylene alkylphenyl ethers, polyoxyethylenesorbitane fatty acid esters, glycol fatty acid esters and the like, oils such as hydrocarbons, silicones, lanolin derivatives, olive oil, hardened castor oil, esters, and the like, solvents such as ethanol, ethylene glycol, 1,3-butyleneglycol, propylene glycol, glycerine, polyethylene glycol and the like, bactericides, preservatives, colorants, thickeners and the like.

The present invention is described in more detail by way of examples and synthetic examples, which should not be construed as limiting the present invention thereto.

Synthetic Example 1

Preparation of Decomposition Derivatives by oxidation of Keratin Material (a) Ten grams of wool fibers were immersed in 700 g of an aqueous 8% peracetic acid solution at room temperature for 1 day to carry out the oxidation reaction. The resulting oxidized wool fibers were filtered, washed with water and immersed in 700 g of a 0.1N ammoniacal solution at room temperature for 1 day, permitting about 90% of the wool to dissolve in the ammoniacal solution. About 1 g of the insoluble matters were removed by filtration and the aqueous ammoniacal solution of keratose to be an oxidized decomposition product of the wool keratin was admixed with 2N hydrochloric acid to adjust the pH to 4.0, whereupon α-keratose was settled as precipitate. This precipitate was filtered, washed with acetone and dried to obtain 5.4 g of u-keratose.

(b) Wool fibers were heated under pressure in an autoclave by the use of a saturated steam of 6 kg/cm$^2$ for 6 minutes and were abruptly released in the air to obtain a porous puffed product. Ten grams of the puffed product which had been reduced into pieces, 250 g of formic acid, and 50 g of 30% aqueous hydrogen peroxide solution were charged into a 500 m three neck flask to immerse the pieces at room temperature for 1 day, whereupon no powder was found in the solution but foam-like masses were floated in the upper layer. This reaction mixture was filtered and the filtrate was poured into 1.5 liters of water, followed by adding hydrochloric acid to adjust the pH to 4. The resulting precipitate was collected by filtration and washed with 500 m of water to obtain 4.5 g of u-keratose. To the insoluble matter from which the reaction product had been removed by filtration were added 350 m of water and then an ammoniacal solution to adjust the pH to 11, permitting the matter to be immersed at room temperature for 1 day. The system was filtered and hydrochloric acid was added to the filtrate to adjust the pH to 4. The resulting precipitate was collected by filtration to obtain 0.7 g of α-keratose. 1.4 g of the insoluble matter was found to be primarily made of β-keratose.

Synthetic Example 2

Preparation of Reduced Decomposition Derivatives of Keratin Materials (a) Ten grams of wool fibers were immersed in 600 ml of an aqueous solution with concentration of 8M urea and 0.01M tris buffer, to which was added 6 ml of 2-mercaptoethanol, followed by adjusting the pH to 10 by means of a 5N potassium hydroxide aqueous solution to effect the reduction reaction in a stream of nitrogen at room temperature. About 3 hours after commencement of the reaction, the wool dissolved in the reaction solution in an amount of about 85% thereof. While the system was adjusted with a 5N potassium hydroxide solution so that the pH was not below 7, 16.5 g of iodoacetic acid was gradually added and the pH of the system was finally adjusted to 8.5 to carry out the carboxymethylation reaction at room temperature for 2 hours. The reaction solution was filtered to remove insoluble matters therefrom and the resultant filtrate was charged into a cellulose tube wherein it was dialyzed against ion-exchanged water to remove low molecular weight impurities including urea. As the urea was dialyzed, the content in the cellulose tube became cloudy since water-insoluble HGT (component with high contents of glycerine and tyrosine was caused to precipitate. After completion of the dialyso HGT was centrifugally removed and S-carboxymethyl keratin (SCMKA) was obtained from the neutral transparent solution of SCMK by the isoelectric precipitation method. That is, 1N hydrochloric acid was added to the system to adjust its pH to 4.4 by which SCMKA became insoluble and separated as precipitate. This precipitate was filtered, washed with ethanol and dried to obtain 4.2 g of SCMKA.

(b) The procedure of Synthetic Example 2 (a) was repeated except that there was used instead of wool fibers feathers which were heated for 6 minutes in an autoclave by means of a superheated steam of 6 kg/cm$^2$ and 240° C. and then abruptly released in the air to obtain a porous puffed product and that 1.75 g of maleic acid was used instead of iodoacetic acid, thereby obtaining 5.3 g of S-(1,2-dicarboxyethyl)-keratin.

(c) The procedure of Synthetic Example 2 (a) was repeated using a powder of hoof of horse instead of wool fibers and 11 g of acrylic acid instead of iodoacetic acid, thereby obtaining 4.2 g of S-(2-carboxyethyl)-keratin.

(d) The procedure of Synthetic Example 2 (a) was repeated using 28 g of styrenesulfonic acid instead of iodoacetic acid thereby obtaining 4.8 g of S-(sulfophenylvinyl)-keratin.

(e) Eight grams of wool fibers were dispersed in 300 ml of n-propanol and 300 m of a 0.1N tris buffer solution. After substitution with nitrogen, 3.2 m of tri-n-butylphosphine was added, followed by agitating at room temperature for 24 hours. The solution was subjected to filtration and to the resulting insoluble matter were added 400 ml of water, 9.28 g of maleic acid and about 30 of 5N potassium hydroxide to adjust the pH to 8.0, followed by agitating at room temperature for 6 hours. To the reaction system was added about 20 ml of a 28% aqueous ammoniacal solution to adjust the pH to 11.5, after which it was agitated for further 18 hours at room temperature. The reaction solution was filtered to remove insoluble matters therefrom and the resultant filtrate was placed into a cellulose tube in which it was dialyzed against ion-exchanged water to remove low molecular weight impurities therefrom. After completion of the dialysis, the insoluble matters in the cellulose tube were removed by centrifugal separation and the resulting neutral transparent aqueous solution was adjusted in pH to 4.4 by addition of about 5.5 ml 1 N hydrochloric acid and the resulting precipitate was collected by filtration, washed with ethanol and dried to obtain 3.9 g of S-(1,2-dicarboxyethyl)-keratin.

(f) The procedure of Synthetic Example 2 (e) was repeated except that there was used instead of wool fibers a powder of a porous puffed product which had been obtained by heating wool in an autoclave by means of a saturated steam of 6 kg/cm$^2$ for 6 minutes and releasing the heated wool in the air abruptly and that 16.5 g of 2-acrylamido-s-methylpropanesulfonic acid was used instead of maleic acid, thereby obtaining 4.5 g of keratin-S-(2-acrylamido-2-methylpropanesulfonic acid).

Synthetic Example 3

Preparation of Hydrolysis Derivatives of Keratin Materials (a) Ten grams of wool fibers were immersed in 300 g of a 1% sodium hydrogensulfite aqueous solution, whose pH was adjusted to 6.7 by the use of a 5N aqueous caustic soda solution. Thereafter, 0.2 g f papain was added to the system to effect the hydrolysis reaction at 60° C. for 15 hours, by which about 80% of the wool dissolved. Insoluble matters were removed by filtration and the sulfite in the resulting filtrate was removed by the ultrafiltration technique using a membrane with a fractional molecular weight of 500. The aqueous solution of the hydrolysate was concentrated and freeze dried to obtain 7.7 g of the hydrolysate having a molecular weight of 500 to 2,000.

(b) Ten grams of wool fibers were immersed in 300 g of a 75% phosphoric acid aqueous solution and the hydrolysis reaction was carried out at 120° to 130° C. for 5 hours. The reaction system was cooled and filtered to remove insoluble matters therefrom, to which was added water of 4 to 5 times in volume of the filtrate to further remove insoluble matters. Then, calcium carbonate or arium hydroxide was added to the filtrate to adjust its pH to 6.7, after which the resulting precipitate was collected by filtration and dried to obtain 8.0 g of a hydrolysate having a molecular weight of 500 to 2,000. Note: The amount of S-S bonds in the hydrolysate obtained by the procedure of Synthetic Example 3 (a) or 3 (b) was 50 moles per $10^5$ g of the hydrolysate, revealing that little or no cystine was destroyed during the course of the hydrolysis.

(c) One hundreds grams of feathers were heated under pressure in an autoclave for 6 minutes by the use of a superheated steam of 6 kg/cm$^2$ and 240° C. and then abruptly released in the air to obtain a porous puffed product. This product was reduced into pieces, to which was added 3 of 0.3N caustic soda for conducting the hydrolysis reaction at 60° C. for 18 hours, followed by neutralizing with 1N hydrochloric acid and filtering the reaction solution. The sodium chloride in the resulting filtrate was removed by the ultrafiltration method using a membrane with a fractional molecular weight of 500. The aqueous solution of the hydrolysate of keratin was concentrated and freeze dried to obtain 7.2 g of the hydrolysate of the keratin. The molecular weight of the hydrolysate was found to be 1,800 when determined by the gel filtration method.

(d) 100 g of pieces of horse's hoof with a uniform size of 0.25 to 1 mm were defatted with a 50% methanol and 50% chloroform solution and then treated with a 1% ammoniacal solution to remove soluble proteins therefrom, which was then placed in a three neck flask, followed by adding 20 g of sodium hydroxide and 400 g of ion-exchanged water and subjecting to the hydrolysis reaction at 90° C. for 4 hours while agitating. After cooling, hydrochloric acid was added to adjust the pH to 8 and the reaction solution was filtered. The sodium chloride in the filtrate was removed, followed by repeating the procedure of Synthetic Example 3 (c) to obtain 68 g of a hydrolysate of the keratin. This hydrolysate had a molecular weight of 2,500 when determined by the gel filtration method.

EXAMPLE 1

Hair treatments (set lotions) of the following formulations were prepared and the texture of the hair treated therewith and the set retention effect were checked. The results are as shown in Table 1.

Formulation:

| | |
|---|---|
| Decomposition derivatives of keratin (or comparative compound) (Table 1) | 1.0% |
| Cationic polymer (Polymer JR400) | 1.0 |
| Sodium chloride | 1.0 |
| Ethanol | 5.0 |
| Water | balance |
| pH | (7.0) |

Tests:

(1) Texture of Treated Hair

A hair tress having a length of 20 cm and a weight of 20 g and made of Japanese female hair was applied with 2 g of each hair treatment over the entirety of the tress and then rinsed with running water of 40° C. for 1 minute, after which the rinsed hair was organoleptically evaluated. The organoleptic evaluation was conducted by the paired comparison technique using as reference the hair which was treated with a commercially available hair rinse comprised mainly of a quaternary ammonium salt and hydrocarbons according to the following evaluation standard. (In the table, average values of 20 expert panel members are indicated.)

| Evaluation Point | Evaluation |
|---|---|
| +2 | Better in texture than the reference hair tress |
| +1 | Slightly better |
| 0 | Equal |
| −1 | Slightly poorer |
| −2 | Poorer |

(2) Set Retention Effect

A hair tress made of Japanese female hair and having a length of 20 cm and a weight of 5 g was satisfactorily applied with each hair treatment and then rinsed with running water of 40° C. for 1 minute, followed by absorbing excess water on the hair with a filter paper. The tress was wound about a glass tube of 1.5 cm in diameter to have a winding width of 5 cm and then fixed at opposite sides thereof. The wound tube was allowed to stand under conditions of 65 R. H. % and 20° C. for 24 hours for curling, followed by removing the curled tress after 24 hours and vertically suspending to measure length of the suspended tress. The degree of the curling was calculated according to the following equation:

$$\text{Degree of Curling (\%)} = \frac{A - (B - A)}{A} \times 100$$

A: Length of the tress immediately after removal
B: Length of the tress 12 hours after removal (3) Measurement of Combing Force in Wet State After evaluation of the texture of the hair tress, it was set in a strain gauge, and was combed with a nylon comb twenty times to measure resisting forces. The average of the measured forces was determined as a combing force.

(4) Measurement of Combing Force in Dry State

After evaluation of the texture and measurement of the combing force in wet state, the hair tress was air dried and evaluated according to the procedures of (1) and (3).

TABLE 1

| Decomposition Derivative of Keratin (or Comparative compound) | Texture of hair | Degree of curling | Combing force Wet | Dry |
|---|---|---|---|---|
| Products of Invention | | | | |
| Decomposition derivative of keratin of Synthetic Example 3 (a) | +1.9 | 80% | 171(g) | 196 |
| Decomposition derivative of keratin material of Synthetic Example 1 (a) | +1.8 | 92% | 200 | 201 |
| Decomposition derivative of keratin material of Synthetic Example 2 (a) | +1.8 | 95% | 231 | 212 |
| Comparative Compounds | | | | |
| Chitosan | +0.8 | 72% | 251 | 300 |
| hydrolysate of collagen (MW = 1,000) | −0.1 | 61% | 303 | 371 |
| Polyvinyl alcohol (MW = 100,000) | +0.1 | 53% | 371 | 453 |
| Acrylic and methacrylic polymer (MW = 17,000) | −1.2 | 50% | 457 | 631 |

EXAMPLE 2

Hair treatments of the following formulations were prepared to check their stability and set retentitivity. The stabilizing effect was determined by storing each treatment at 25° C. for 1 month after the preparation and judging the state of the stored treatment according to the following standard. The set retentivity was determined in the same manner as in Example 1. The results are shown in Table 2 below.

| | |
|---|---|
| Decomposition derivative of keratin (Table 2) | 1.0% |
| Cationic polymer (Table 2) | 1.0 |
| Water-soluble salt (or hydrotrope) | 1.0 |
| Water | balance |
| pH | (7.0) |

TABLE 2

| Decomposition derivative of keratin | Cationic polymer | Water-soluble salt (or hydrotrope) | Stability (25° C.) | Curl-retaining effect (%) |
|---|---|---|---|---|
| Composition of Invention | | | | |
| Derivative of Synthetic Example 3 (a) | Merquat 550 | Sodium chloride | O | 93 |
| Derivative of Synthetic Example 3 (a) | Gafquat 734 | Urea | O | 95 |
| Derivative of Synthetic Example 1 (a) | Merquat 550 | Sodium chloride | O | 92 |
| Derivative of Synthetic Example 1 (a) | Gafquat 734 | Potassium hydrogenphosphate | O | 89 |
| Derivative of Synthetic Example 2 (a) | Merquat 550 | Sodium chloride | O | 90 |
| Derivative of Synthetic Example 2 (a) | Gafquat 734 | Aluminum chloride | ⊚ | 87 |
| Comparative Composition | | | | |
| Derivative of Synthetic Example 3 (a) | Polymer JR 400 | Ethanol | x | 68 |
| Derivative of Synthetic Example 1 (a) | Polymer JR 400 | Glycerine | x | 62 |
| Derivative of Synthetic Example 2 (a) | Polymer JR 400 | — | x | 52 |

Evaluation Standard (Stability)
O stable
⊚ turbid
x isolated

EXAMPLE 3

Shampoo Composition

The following ingredients were mixed to give a shampoo composition. The shampoo composition exhibited excellent texture, set retentivity and stability.

| | | |
|---|---|---|
| 1. | Triethanolamine lauryl sulfate | 10.0% |
| 2. | Decomposition derivative of keratin obtained in Synthetic Example 1 (a) | 0.5 |
| 3. | Merquat 550 | 0.5 |
| 4. | Sodium chloride | 2.0 |
| 5. | Water | balance |
| | pH | (6.5) |

EXAMPLE 4

Hair Rinse Composition

The following ingredients were mixed to obtain a hair rinse composition. The composition showed an excellent rinsing effect to give fireness and stiffness to the hair and its stability was good.

| | | |
|---|---|---|
| 1. | Cetyltrimethylammonium chloride | 3.0% |
| 2. | Decomposition derivative of keratin obtained in Synthetic Example 2 (a) | 1.0 |
| 3. | Polymer JR 400 | 1.0 |
| 4. | Sodium chloride | 3.0 |
| 5. | Water | balance |
| | pH | (7.0) |

EXAMPLE 5

Hair Treatment Composition

The following ingredients were mixed to obtain a hair treatment. The composition exhibited excellent texture when applied to hair and imparted firmness and stiffness to hair.

| 1. | Polyoxyethylene (20) sorbitan monooleate | 5.0% |
|---|---|---|
| 2. | Silicone | 5.0 |
| 3. | Decomposition derivative of keratin obtained in Synthetic Example 3 (a) | 1.2 |
| 4. | Merquat 550 | 0.5 |
| 5. | Sodium sulfate | 2.0 |
| 6. | Water | balance |
|  | pH | (7.0) |

EXAMPLE 6

Hair Setting Lotion

The following ingredients were mixed to give a hair setting lotion, exhibiting an excellent setting effect.

| 1. | Ethanol | 10.0% |
|---|---|---|
| 2. | Decomposition derivative of keratin obtained in Synthetic Example 2 (a) | 2.0 |
| 3. | Polymer JR 400 | 1.0 |
| 4. | Methylparaben | 0.5 |
| 5. | Methyl cellulose | 0.5 |
| 6. | Sodium chloride | 2.5 |
| 7. | Water | balance |
|  | pH | (7.2) |

What is claimed is:

1. A hair treatment composition comprising the following three ingredients (A), (B) and (C):

(A) 0.05 to 10 wt. % of at least one decomposition derivative of keratin having a molecular weight in the range of 30,000–100,000 and being selected from the group consisting of (1) decomposition products obtained by oxidation of keratin, and (2) derivatives at the thiol groups of decomposition products obtained by reduction of keratin, said keratin being obtained from animal hairs, human hairs, features, nails, horns, hooves or scales;

(B) 0.05 to 10 wt. % of a cationic polymer having an average molecular weight of 500–5,000,000 and being selected from the group consisting of quaternize derivatives of cellulose ethers, allyl quaternary ammonium homopolymers of the recurring units of formulas (I) and (II):

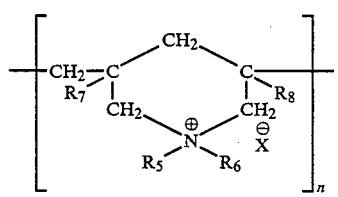

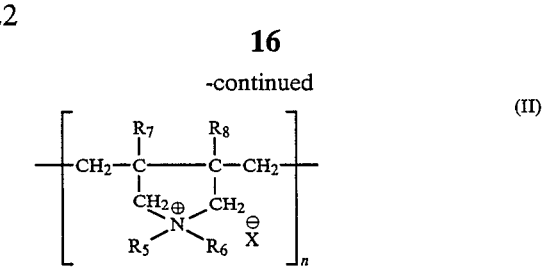

in which $R_5$ and $R_6$ are the same or different and represent hydrogen or an alkyl group having 1 to 18 carbon atoms, $R_7$ and $R_8$ are the same or different and independently represent hydrogen, an alkyl group having 1 to 3 carbon atoms, or phenyl group, $X^-$ represents chloride or bromide, sulfate, nitrate, methyl sulfate and hydroxycarbonate and n has a value sufficient to give a molecular weight of 10,000–1,000,000; polymers of the recurring units of the formulas (III) and (IV):

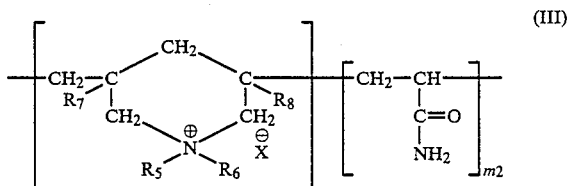

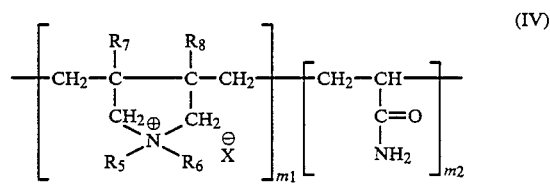

in which $m_1$ and $m_2$ are values sufficient to give a molecular weight of 10,000–1,000,000, and $R_5$, $R_6$, $R_7$, $R_8$ and $X^-$ have the same meanings as defined above; polymers of the formula (V):

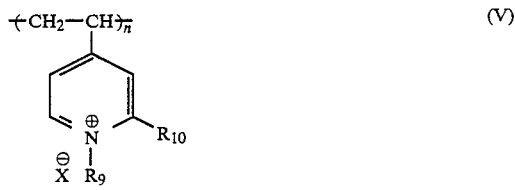

in which $R_9$ and $R_{10}$ are the same or different and independently represent hydrogen, an alkyl group having 1 to 6 carbon atoms, or a phenyl group, and n and X have the same meanings as defined hereinbefore, and quaternized derivatives of copolymers of N-vinylpyrrolidone/vinyl monomer of the formula (VI):

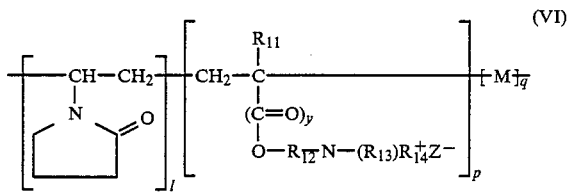

in which l, p and q are values selected from the group of values such that the monomer units in the respective brackets are, respectively, 20 to 99 mole %, 1 to 80 mole % and 0 to 50 mole %, y is 0 or 1, $R_{11}$ represents a hydrogen atom or methyl group, $Rl_2$ represents

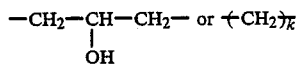

wherein k is a value of 2 to 18, $R_{13}$ represents an alkyl group having 1 to 4 carbon atoms, $RI_4$ represents methyl, ethyl, or benzyl, Z represents chloride, bromide, iodide, $SO_4$, $HSO_4$ or $CH_3SO_3$, and M represents a monomer unit of a copolymerizable vinyl monomer; and (c) 0.01 to 10 wt. % of at least one compound selected from the group consisting of aluminum sulfate, barium chloride, calcium carbonate, calcium chloride, magnesium nitrate, magnesium sulfate, copper sulfate, potassium phosphate, potassium thiocyanate, sodium chloride, lithium chloride, ammonium bicarbonate, ammonium nitrate, sodium sulfate, sodium lactate, sodium benzoate, sodium citrate and urea.

2. The hair treatment composition according to claim 1, wherein said ingredient (A) is contained in amount of 0.1 to 2% by weight of the composition.

3. The hair treatment composition according to claim 1, wherein said ingredient (B) is contained in an amount of 0.1 to 2% by weight of the composition.

4. The hair treatment composition according to claim 1, wherein said ingredient (C) is contained in amount of 0.1 to 3% by weight of the composition.

5. The hair treatment composition according to claim 1, wherein $R_{13}$ is a methyl, ethyl or t-butyl group.

* * * * *

UNITED STATES PATENT AND TRADEMARK OFFICE
CERTIFICATE OF CORRECTION

PATENT NO. : 4,895,722

DATED : JANUARY 23, 1990

INVENTOR(S) : YOSHIAKI ABE ET AL

It is certified that error appears in the above-identified patent and that said Letters Patent is hereby corrected as shown below:

In Claim 1, column 15, line 51, delete "features" and insert --feathers--.

In Claim 1, column 15, line 56, delete "allyl" and insert --diallyl--.

In Claim 1, column 16, line 55, delete "X" and insert --$X^-$--.

In Claim 1, column 17, line 13, delete "$RI_4$" and insert --$R_{14}$--.

Signed and Sealed this

Twenty-fifth Day of February, 1992

Attest:

HARRY F. MANBECK, JR.

*Attesting Officer*  *Commissioner of Patents and Trademarks*